United States Patent
Garde et al.

(10) Patent No.: US 6,557,421 B2
(45) Date of Patent: May 6, 2003

(54) MANDREL SUPPORTED TENSILE TEST TO EVALUATE WELD BONDING

(75) Inventors: Anand M. Garde, West Simsbury, CT (US); Gerald D. Boyer, Hillsboro, MO (US); John F. Kraus, Hillsboro, MO (US); Peter M. Hess, Hillsboro, MO (US)

(73) Assignee: Westinghouse Electric Company LLC, Pittsburgh, PA (US)

( * ) Notice: Subject to any disclaimer, the term of this patent is extended or adjusted under 35 U.S.C. 154(b) by 0 days.

(21) Appl. No.: 09/901,459

(22) Filed: Jul. 9, 2001

(65) Prior Publication Data
US 2002/0007683 A1 Jan. 24, 2002

Related U.S. Application Data
(60) Provisional application No. 60/219,683, filed on Jul. 21, 2000.

(51) Int. Cl.[7] .................................................. G01N 3/20
(52) U.S. Cl. ........................................... 73/850; 73/851
(58) Field of Search .......................... 73/850, 851, 826, 73/827, 856, 831

(56) References Cited

U.S. PATENT DOCUMENTS

| | | | | | |
|---|---|---|---|---|---|
| 2,884,986 | A | * | 5/1959 | Heldenbrand | 72/302 |
| 4,147,215 | A | * | 4/1979 | Hodge et al. | 166/380 |
| 4,516,431 | A | * | 5/1985 | Heldenbrand | 73/826 |
| 6,116,118 | A | * | 9/2000 | Wesch, Jr. | 81/57.16 |

FOREIGN PATENT DOCUMENTS

| | | | | |
|---|---|---|---|---|
| EP | 568840 A1 | * | 11/1993 | G01N/3/04 |
| JP | 54155143 A | * | 12/1979 | B23K/11/04 |

* cited by examiner

*Primary Examiner*—Hezron Williams
*Assistant Examiner*—Lilybett Martin

(57) ABSTRACT

A tensile test apparatus and method for testing a circumferential weld on a tubular member wherein the tube region of the weld is completely supported by a mandrel and the tubular specimen is gripped on both sides of the weld along the specimen's longitudinal length with a very small separation distance between the tensile test grips. If there are any non-bonded defects in the weld, they are captured by the weld fracture surface as mesa or void features with an orientation different from that of a well bonded region.

7 Claims, 2 Drawing Sheets

MANDREL SUPPORTED TENSILE TEST TO EVALUATE WELD BONDING

CROSS-REFERENCE TO RELATED APPLICATION

The present application claims priority of U.S. Provisional Patent Application Ser. No. 60/219,683 which was filed Jul. 21, 2000, entitled "MANDREL SUPPORTED TENSILE TEST TO EVALUATE WELD BONDING FOR NUCLEAR FUEL ROD END CAP WELDS".

BACKGROUND OF THE INVENTION

1. Field of the Invention

This invention relates generally to metallurgical testing of weld joints and more particularly, to a destructive tensile test to evaluate a tubular weld joint.

2. Related Art

Where a number of different welds are being applied under identical conditions such as on an assembly line, it is desirable to periodically take a sample to test the quality of the weld. Radiological and ultrasonic nondestructive techniques have been employed in the art in the past for this purpose. Where the integrity of the weld is important for the application, especially where safety considerations are involved, it is desirable to perform a more exacting test on the periodic samples to confirm the integrity of the metallurgical bond. Such is the case in the manufacture of nuclear fuel rods formed from a tubular cladding that is welded to an end cap. In the case of a nuclear fuel rod, it has not been practical to perform a tensile fracture test to test the weld, because the weld microstructure has a higher strength than the cladding. As a result, tensile fracture of the unsupported cladding tube weld specimen is always in the tube region away from the weld. Such a fracture location is unable to capture non-bond regions of the weld (if they were to exist) on the fracture surface. Introduction of a notch at the weld bond line on the tube outer surface to induce failure in the weld is cumbersome and does not always consistently localize fracture in the weld region. For that reason, current practice is to employ a metallographic evaluation of weld bonding which provides weld bonding data for a single cross section of the weld and not the entire circumference. Metallographic examination of weld specimens involves specimen sectioning, polishing, acid etching and disposal of the acid waste. The steps for metallographic evaluation require significant effort, expense and time.

Accordingly, it is an object of this invention to provide a method and apparatus that provides a faster and less costly examination of a weld's metallurgical structure on a tubular member that distinctively contrasts well bonded regions from unbonded regions in the weld. It is a further object of this invention to provide such an apparatus and method that examines the entire weld circumference.

SUMMARY OF THE INVENTION

These and other objects are achieved by the method and apparatus of this invention which provides a tensile test for a tubular member that initiates failure in a circumferential weld. The tube region immediately on one side of the weld is completely supported by a mandrel and the specimen is gripped on either side of the weld along the longitudinal axis of the tube. In the preferred embodiment, a very small separation distance is maintained between the mandrel supporting the tube region on one side of the weld and the gripping mechanism supporting the specimen on the other side of the weld. A force is applied to one or both of the tensile grips in a direction away from the weld along the longitudinal axis of the tube to initiate failure in the weld. If there are any non-bond defects in the weld, they are captured by the weld fracture surface as mesa or void features with an orientation different from that of a fracture of a well bonded region. The fracture surface orientation for a well bonded region is approximately 45° to the tensile axis, while the fracture orientation of a non-bonded region is approximately perpendicular to the tensile axis. The degree of non-bonding is calculated from the area fraction of fracture surface area showing the distinct non-bond features as revealed by the examination of the fracture surface under a stereomicroscope. The tensile test of this invention evaluates weld bonding over the entire weld circumference and provides weld bonding results on production weld evaluation specimens quickly and with less effort than is required to perform a metallographic examination.

BRIEF DESCRIPTION OF THE DRAWINGS

These and other aspects of the invention will be more fully appreciated from the description of the preferred embodiment set forth hereafter, when read in conjunction with the drawings in which.

DESCRIPTION OF THE PREFERRED EMBODIMENT

Figure 1:
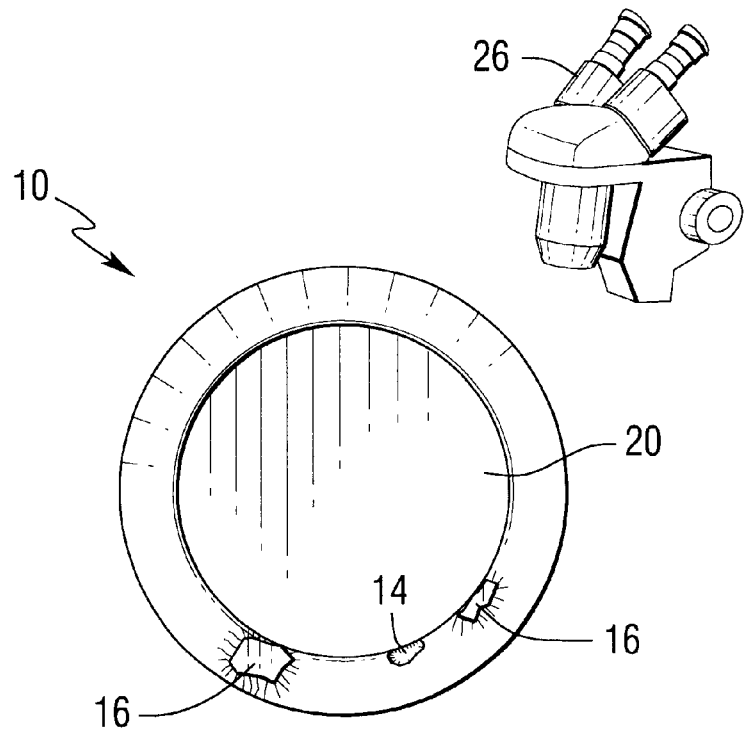
FIG. 1 is schematic view of the fracture surface of a nuclear fuel element weld showing the end cap interface with the cladding tube.
Figure 1:
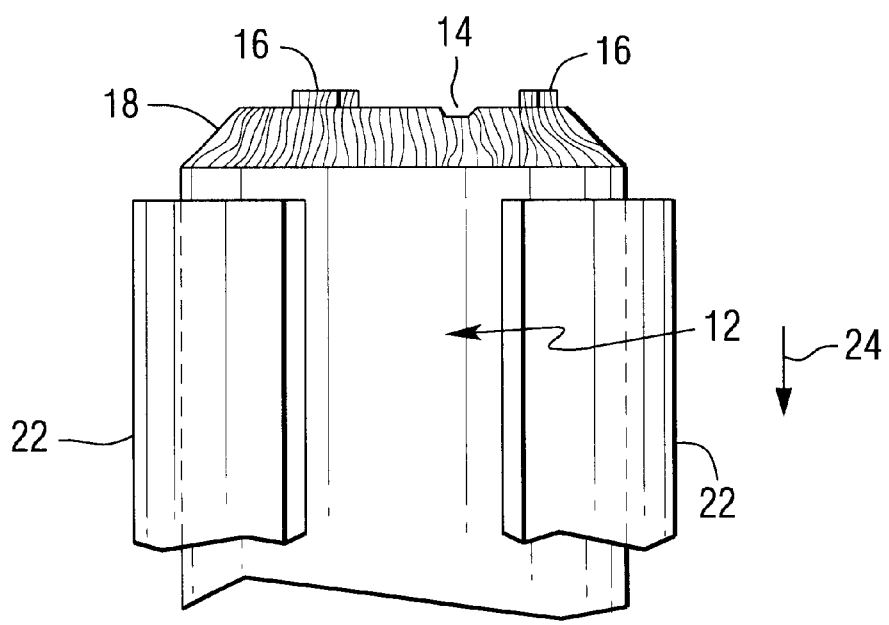

The apparatus and method of this invention are described, in their preferred embodiments, applied to destructively tensile test the weld between a fuel element cladding 10 and its end cap 12, illustrated in FIG. 1. Fuel elements are typically hollow tubes constructed of a material having a low neutron capture cross section, such as Zircaloy. The hollow tubes house a tandem array of partially enriched Uranium Dioxide fuel pellets. The pellets are stacked to a given height within the fuel element cladding and the remaining area forms a plenum for the collection of fission gasses that are generated during reactor operation. The plenum is sealed by an end cap 12, which is welded to the cladding 10 at their interface. In this embodiment, a magnetic force welding process is used for this purpose. A high integrity weld is necessary to assure that the fission gasses do not leak into the reactor coolant. This invention provides a tensile test to destructively test samples taken from a production line to assure that the production welds performed under identical conditions will maintain that integrity.

Figure 2:
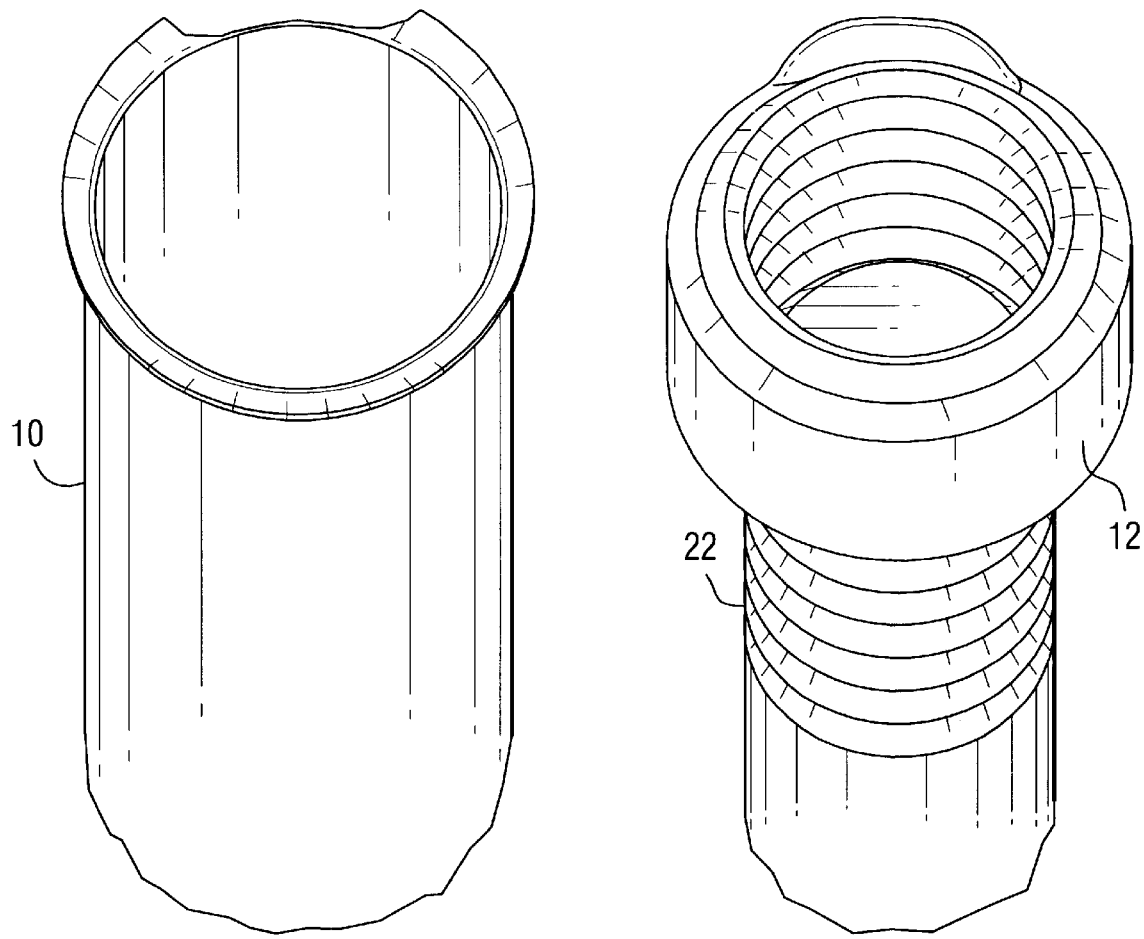
FIG. 2 is a perspective view of a fuel element cladding and end cap after the tensile test was performed revealing a well bonded region.

In accordance with this invention, a mandrel 20 is inserted into the cladding 10 to a depth where it just about touches a protruding plateau on the end cap (not shown in FIG. 1). The mandrel 20, thus positioned, grips and supports the interior cladding wall just below the weld. The end cap is also gripped on the other side of the weld by a gripping mechanism 22 and a force 24 is exerted to either gripping mechanism 20 and/or 22 in opposite directions away from the weld and parallel to the axis of the tubular cladding until the weld fails. If the end cap 12 is large enough, the gripping mechanism 22 may be applied to the outside of the end cap as shown in FIG. 1. However, if the end cap does not have a large enough surface to grip, a hole can be drilled in the end cap, the hole threaded and a gripper 22 with a complementary thread can be threaded into the end cap until it approaches and just about touches the mandrel location as shown in FIG. 2. Though not required in the embodiment illustrated in FIG. 1, preferably a very small separation distance along the longitudinal dimension of the tube is maintained between the grippers 20 and 22 with each gripper positioned on either side of the weld.

A weld specimen with a full support mandrel in the tube region touching the end cap pedestal and a proper gripping of the specimen on two sides of the bond line with a minimum grip separation along the longitudinal length of the fuel element consistently induces failure in the weld. This was confirmed by 406 weld tensile tests (259 tests on Zircaloy-4 pressurized water reactor fuel rod welds and 147 Zircaloy-2 boiling water reactor fuel rod welds) where a failure in the weld was obtained. The measured degree of weld bonding on these tensile tests correlated very well with the degree of weld bonding measured by metallography on a comparable number of weld specimens fabricated under identical conditions.

If there are any non-bond defects in the weld, they are captured by the weld fracture surface as mesa (shown in FIG. 1 by reference character 16) or void (shown in FIG. 1 by reference character 14) features with an orientation different from that of a fracture of a well bonded region. The fracture surface orientation for a well bonded region is approximately 45° to the tensile axis as shown in FIGS. 1 and 2. In contrast, the fracture orientation of a non-bonded region is approximately perpendicular to the tensile axis as shown in FIG. 1. The degree of non-bonding is calculated from the area fraction of fracture surface area showing the distinct non-bonded features as revealed by the examination 26 of the fracture surface under a stereomicroscope. Bond region fracture surfaces have a grainy dull appearance with an orientation approximately 45° to the tensile axis, as mentioned above. The non-bond regions of the fracture surface have a shiny appearance of either a machined weld prep surface of the tube end/end cap or a solidified molten material heated during welding but not bonded to the other mating surface. The orientation of the non-bond region is significantly different from the 45° to the tensile axis orientation, the plane of maximum shear stress.

Thus, the method and apparatus of this invention provide a tensile test that evaluates weld bonding over the entire weld circumference compared with the metallographic technique that evaluates bonding in a specific cross section of local orientation on the weld circumference. The tensile test of this invention provides weld bonding results on the production weld evaluation specimens quickly and with less effort and expense compared to the metallographic technique and does not generate acid waste.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. A method for tensile testing an end cap weld in a tube region of an elongated nuclear fuel element specimen having a weld, comprising the steps of:
    a. gripping the specimen with a mandrel at a first position on a first axial side of the weld, in the tubular region in close proximity of the weld;
    b. gripping the specimen with a gripping means at a second position on a second axial side of the weld along the longitudinal dimension of the specimen, wherein the first and second positions are in close proximity to each other on either side of the weld in the longitudinal direction of the tubular specimen;
    c. causing tensile failure in the specimen by exerting a force in the axial direction away from the weld; and
    d. observing a weld fracture surface for distinct defects characteristic of a non-bonded region.

2. The method of claim 1 wherein the observing step includes the step of identifying on the weld fracture surface mesas and voids with an orientation different from that of a fracture of a well bonded region, wherein the orientation of the well bonded region is approximately 45 degrees to the tensile axis.

3. The method of claim 1 including the step of calculating the degree of non-bonding from the area fraction of weld fracture surface showing the distinct defects.

4. The method of claim 1 wherein the step of observing is carried out for substantially the entire weld circumference.

5. An apparatus for conducting a tensile test to initiate failure in an end cap weld in an elongated nuclear fuel element specimen having an axial dimension, comprising:
    a. a mandrel for supporting a tube region of the specimen on a first axial side of the weld adjacent the weld;
    b. means for gripping the specimen on a second axial side of the weld adjacent the weld;
    c. means for causing tensile fracture of the tube region to detect non-bond defects, wherein the defects are observable directly from the weld fracture surface; and
    d. means for calculating the degree of non-bonding from the area fraction of the fracture surface area showing non-bonding to quantify the defects.

6. An apparatus for conducting a tensile test to initiate failure in an end cap weld in an elongated nuclear fuel element specimen having an axial dimension, comprising:
    a. a mandrel for supporting a tube region of the specimen on a first axial side of the weld adjacent the weld;
    b. means for gripping the specimen on a second side of the weld adjacent the weld wherein a portion of the specimen on the second side of the weld is internally threaded and the means for gripping is a member having a thread formed around at least a portion of its circumference that is complementary to the thread on the portion of the specimen on the second side of the weld; and
    c. means for causing tensile fracture of the tube region to detect non-bond defects, wherein the defects are observable directly from the weld fracture surface.

7. The apparatus of claim 6 wherein the portion of the specimen on the second side of the weld is an end cap to the tubular specimen.

* * * * *